United States Patent
Khumtaveeporn et al.

(10) Patent No.: US 6,271,005 B1
(45) Date of Patent: Aug. 7, 2001

(54) ENZYMATIC RESOLUTION OF AMINOTETRALINS

(75) Inventors: Kanjai Khumtaveeporn, Aurora; Trina Cherryle Cosway, North York; Wen-Lung Yeh, Thornhill, all of (CA)

(73) Assignee: Torcan Chemical Limited, Ontario (CA)

( * ) Notice: Subject to any disclaimer, the term of this patent is extended or adjusted under 35 U.S.C. 154(b) by 0 days.

(21) Appl. No.: 09/567,375

(22) Filed: May 10, 2000

(30) Foreign Application Priority Data

Jan. 5, 2000 (CA) .................................................. 2307390

(51) Int. Cl.[7] .................................................. C12P 13/00
(52) U.S. Cl. .......................................... 435/128; 564/202
(58) Field of Search .............................. 435/128; 564/202

(56) References Cited

U.S. PATENT DOCUMENTS

| | | |
|---|---|---|
| 4,968,837 | 11/1990 | Manimaran et al. . |
| 5,300,437 | 4/1994 | Stirling et al. . |

FOREIGN PATENT DOCUMENTS

| | | |
|---|---|---|
| 1340332 | 1/1999 | (CA) . |
| 0 385 568 | 2/1990 | (EP) . |
| WO 90/15047 | 12/1990 | (WO) . |

OTHER PUBLICATIONS

Chem Abstract Online 1995:182487, 1995.*
Ames, et al. J. Chem. Soc. (1965) 2636 The Synthesis of Alkoxy–1,2,3,4–tetrahydronaphthalene Derivatives.
Tschaen, et al. J. Org. Chem. (1995) 60, 4324–4330 Asymmetric Synthesis of MK–0499.
Sonesson, et al. J. Med. Chem. (1995) 38, 1319–1329.
Hilver, et al. J. Med. Chem. (1990) 33, 1541–1544.
McDermed, et al. J. Med. Chem. (1976) 19, 547 Synthesis and Dopaminergic Activity of (=)–, (+)–, and (–)–2–Dipropylamino–5–hydroxy–1,2,3,4–tetrahydronaphthalene[1].
Bakthavachalam, et al. J. Med. Chem.(1991) 34, 3235 Florescent Probes for Dopamine Receptors.
Ye, et al. J. Med. Chem. (1989) 32, 478–486 Conformationally Restricted and Conformationally Defined Tyramine Analogues Inhibitors of Phenylethanolamine N–Methyltransferase[1a].
Devocelle, et al. Tetrahedron Letters (1999) 40, 4551–4554 Alternative synthesis of the chiral atypical β–adrenergic phenylethanolaminotetraline agonist SR58611A using enantioselective hydrogenation.
Tillyer, et al. Tetrahedron Letters (1995) 36, No. 25, 4337–4340 Asymmetrric Reduction of Keto Oxime Ethers Using Oxazaborolidine Reagents. The Enantioselective Synthesis of Cyclic Amino Alcohols.
Gmeiner, et al. Tetrahedron Letters (1994) 50, No. 37, 10909–10922 Asymmetric Synthesis of β–Aminotetralins by Electrophilic Amination.
Charlton, et al. Can. J. Chem. (1990) 68, 2028–2032 An asymmetric synthesis of 2–amino–6, 7–dihydroxy–1,2,3, 4–tetrahydronaphtalene (ADTN).
Cecchi, et al. J. Med. Chem. (1994) 29, 259–267 Synthesis and β–adrenergic activity of atypical β–adrenergic phenylethanolaminotetralin stereoisomers.
Norlander, et al. J. Org. Chem. (1985) 50, 3619–3622 A Short Enantiospecific Synthesis of 2–Amino–6, 7–dihydroxy–1,2,3,4–tetrahydronaphthalene (ADTN).
Nichols, et al. J. Med. Chem. (1973) 16, No. 5, 480–483 Asymmetric Synthesis of Psychotomimetic Phenylisopropylamines[1].
Frahm, et al. Tetrahedron Letters (1981) 22, No. 28, 2633–2636 Asymmetric Synthesis of CIS–2–Substituted Cyclohexanamines with High Optical Purity.
Wiehl, et al. Chem. Ber. (1986) 119, 2668–2677 Synthese and absolute Konfiguration 2–substituierter Cyclopentanamine.
Bringmann, et al. Tetrahedron Letters (1989) 30, No. 3, 317–320 Enantiomerically Pure Oxygenated 1–phenylethylamines from Substituted Acetophenones: By Reduction and Amination and Regiospecific Benzylic Cleavage[1].
Bringmann, et al. Synthesis (Communications) (1989) 608–610 A Simple, Chiral–Pool–Independent Synthesis of Enantiomerically Pure Alanine–Derived ⊕–Amino Aldehyde Acetals[1].
Lin, et al. J. Med. Chem. (1993) 36, 1053–1068 Centrally Acting Serotonergic and Dopaminergic Agents.
Audia et al. Tetrahedron Letters (1996) 37 No. 24, 4121–4124 A Diastereoselective Tandem Metalloenamine Alkylation/Aza–annulation of β–Tetralones Expedites the Synthesis of Benzoquinolinones.

* cited by examiner

*Primary Examiner*—Samuel Barts
(74) *Attorney, Agent, or Firm*—Nixon & Vanderhye

(57) ABSTRACT

Stereoisomers of carbocyclic amine compounds such as amino tetralins are separated by subjecting a mixture of the stereoisomers to reaction with an acylating agent in the presence of the enzyme *Pseudomonas capacia* lipase which effect selective acylation of one of the stereoisomers to form a separable amide, whilst leaving the other stereoisomer substantially unchanged.

8 Claims, 1 Drawing Sheet

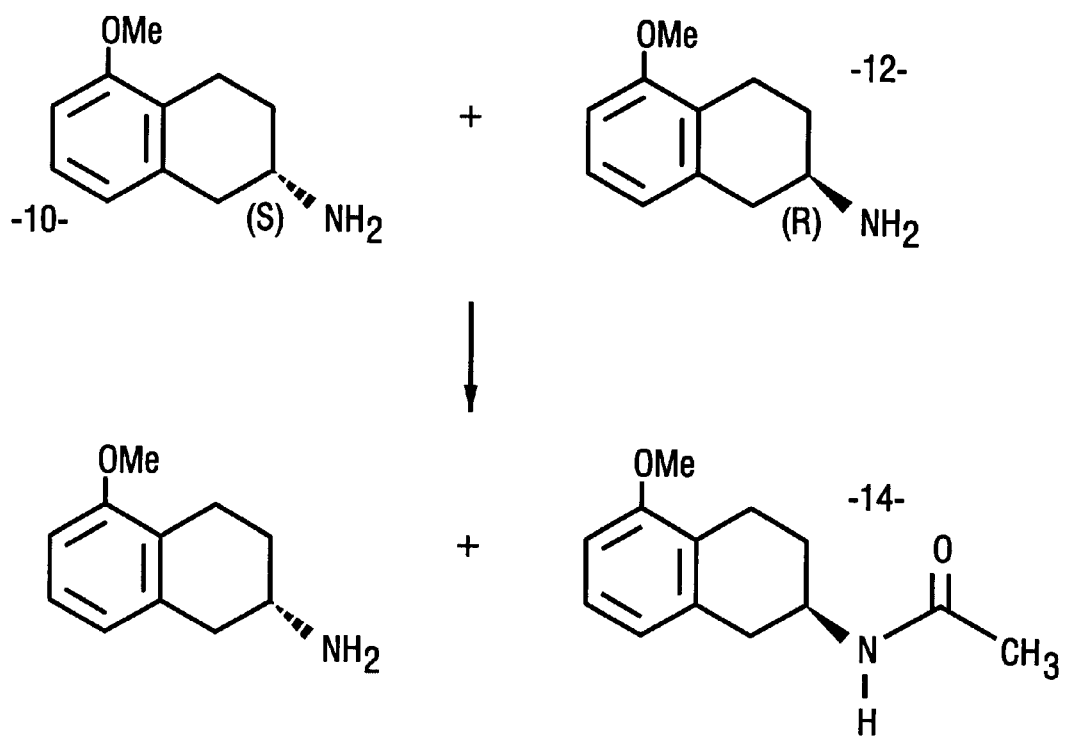

ENZYMATIC RESOLUTION OF AMINOTETRALINS

FIELD OF THE INVENTION

This invention relates to preparation of organic chemical compounds, in particular to preparation of carbocyclic amine compounds. More specifically, it relates to processes for separation of stereoisomers of carbocyclic amine compounds from a mixture containing the different isomers.

BACKGROUND OF THE INVENTION

Carbocyclic amines, in which a primary or secondary amine group is bonded to a carbon of the carbocyclic structure, commonly exhibit chirality, with one of the stereoisomers having a different utility, or a different degree of utility, from the other. Accordingly there is a need for efficient processes for separation of streoisomers of carbocyclic amines.

One class of carbocyclic amines which can exhibit chirality is the aminotetralins. Various 2-aminotetralin compounds are known to exert pharmacological effects on the nervous system of the mammalian body, by binding selectively to 5-HT receptors. One specific such compound, showing promise as an agent for treatment of Parkinson's disease, is N-0923, a chiral 2-aminotetralin-ethylthiophene compound of formula:

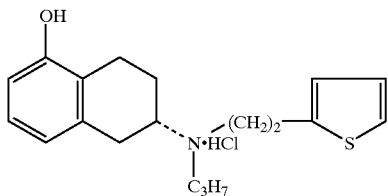

The chirality at C-2 is important in the activity of this and similarly useful 2-aminotetralins, and synthetic methods for its production need to be capable of producing the specific stereoisomer in substantially pure form. A key intermediate in the chemical synthesis of compounds such as N-0923 is (S)-5-alkoxy-2-aminotetralin hydrochloride of formula I:

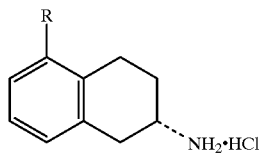

where R represents lower alkoxy (in the specific case of N-0923 preparation, R is methoxy). Producing the substantially pure (S) enantiomer of this intermediate compound is necessary, in the preparation of N-0923 from it.

BRIEF REFERENCE TO THE PRIOR ART

Ames et al., J. Chem. Soc. (1965) 2636 describe the preparation of racemic mixtures of 5-methoxy-2-aminotetralin, by, firstly, reaction of 5-methoxy-2-tetralone with hydroxylamine hydrochloride and sodium hydroxide to convert the 2-oxo group to a 2-hydroxylamine =N—OH) group and secondly, hydrogenation of this product with hydrogen over Raney nickel in the presence of ammonia. No consideration is given to the preparation of specific stereoisomers, or to the separation of the stereoisomers, since these compounds are prepared as part of a synthetic scheme where stereo specificity is unimportant.

U.S. Pat. No. 5,300,437 Sterling et al., describes a process for stereos elective synthesis of chiral amines, such as 2-amino-5-methoxytetralin, in which a corresponding ketone is contacted with an omega-amino acid transaminase in the presence of an amino donor. However, these enzymes are not widely available.

Tschaen et al. J. Org. Chem. 1995, 60, 4324–4330, disclose, as part of a synthetic scheme for preparing stereospecific tetralin compounds substituted with N-heterocycles (MK-0499), a chiral reduction of 5-bromo-2-tetralone to the corresponding chiral 2-alcohol using a yeast (trichosporon capitatum), followed by conversion to the 2-azide and reduction to the 2-amine. This approach is not attractive for scale-up, since the yeast is not commercially available.

The prior art contains other disclosures of preparation of racemic mixtures of aminotetralins, followed by chemical resolution thereof, for example U.S. Pat. No. 4,968,837 Thanikavelu et al., issued Nov. 6, 1990, which shows resolution of substituted aminotetralins with diaroyltartaric acid; Sonesson et al. "Synthesis and Evaluation of Pharmacological and Pharmacokinetic Properties of Monopropyl Analogs of 5-, 7-, and 8-[[(Trifluoromethyl)sulfonyl]oxy]-2-Aminotetralins: Central Dopamine and Serotonin Receptor Activity", J. Med. Chem. 1995, Vol. 38, page 1319–1329, which shows resolution of substituted aminotetralins with 2-chlocyphos (a chiral cyclic phosphoric acid); and Hillver et al. "(S)-5-Fluoro-8-hydroxy-2-(dipropylamino)tetralin: A Putative 5-$HT_{1A}$-Receptor Antagonist", J. Med. Chem., 1990, Vol. 33, pages 1541–1544, which discloses resolution of substituted aminotetralins with tartaric acid. Such process are relatively inefficient, and relatively expensive to operate.

McDermed et.al., "Synthesis and Dopaminergic Activity of (±)-, (+)-, and (−)-2 Dipropylamino-5-hydroxy-1,2,3,4-tetrahydronaphthalene", J.Med.Chem (1976), 19, 547, describe the resolution of aminotetralin derivatives, namely (±)-2-(N)-benzylamino-5-methoxytetralin, by reaction with (−)-mandelic acid. Bakthavachalan et.al., "Fluorescent Probes for Dopamine Receptors: Synthesis and Characterization of Fluorescein and 7-Nitrobenz-2-oxa-1,3-diazol-4-yl Conjugates of D-1 and D-2 Receptor Ligands", J.Med.Chem. (1991), 34, 3235 disclose the resolution of 2-(N-benzylamino)-5-methoxytetralin by reaction with D- and L-ditoluoyltartaric acids. These chemical methods of resolution require repeated recrystallization of the product, which lowers the eventual yield.

SUMMARY OF THE INVENTION

It is an object of the present invention to provide a novel and effective process for the separation of (R)-isomers and (S)-isomers of carbocyclic amines, from a mixture thereof.

The present invention provides a process of selective enzymatic acylation of carbocyclic amines. A mixture of (S) and (R) carbocyclic amines is subjected to reaction with an acylating agent in the presence of the enzyme Chiro CLEC-PC (*Pseudomonas cepacia* lipase). The (R) isomer is selectively acylated, while the (S)-isomer remains substantially unaffected. Accordingly, after the reaction has proceeded to a sufficient extent towards completion, the two isomers can be separated from one another and from the reaction medium by standard physico-chemical methods such as chromatography or acid extraction. Then further chemical reactions can be conducted on the desired isomer (in most cases, the (S)-isomer), to the exclusion of the undesired isomer, to obtain stereospecific final products.

Thus according to the present invention, there is provided a process of extracting a stereoisomer of a carbocyclic amine compound from a mixture containing two or more such stereoisomers, which comprises subjecting the mixture to reaction with an acylating agent in the presence of the enzyme *Pseudomonas cepacia* lipase to effect selective acylation of one said stereoisomer, whilst leaving other said stereoisomers substantially unchanged, and separating the selectively acylated carbocyclic amine stereoisomer from the reaction mixture.

BRIEF REFERENCE TO THE DRAWINGS

The single FIGURE of accompanying drawings is a diagrammatic representation of a preferred embodiment of the process of the present invention.

DESCRIPTION OF THE PREFERRED EMBODIMENTS

Carbocyclic amines to which the present process may be applied are carbocyclic compounds having from 3–10 carbon atoms in alicyclic struture, with an amine group directly bound to a ring carbon atom to form a chiral center thereat. The 3–10 C alicyclic structure may be fused to one or more additional carbocyclic rings, alicyclic or aromatic, and such alicyclic or aromtic rings may be unsubstituted, or substituted with one or more substituents such as lower alkyl, lower alkoxy, halogen, cyano, lower alkylcarbonyl, lower alkoxycarbonyl and the like. "Lower" in this context means $C_1$–$C_6$, in accordance with normal chemical parlance.

Preferred compounds to which the process of the invention is applied are aminotetralins (1,2,3,4-tetrahydronaphthalenes) carrying one or more such substituents on the aromatic portion of the molecule. The particularly preferred compound for isolation according to the present invention is a stereoisomer of 5-methoxy-2-aminotetralin, most preferably the (S)-stereoisomer thereof, since this is the specific stereoisomeric compound useful as an intermediate in preparing the aforementioned pharmaceutically active compound N-0923.

Processes of preparing racemic mixtures of aminotetralins are known in the art, and do not constitute a part of the present invention. The choice and conducting of such processes is within the skill of the art, and the process of the present invention is applicable to separation of stereoisomeric mixtures resulting from any of these processes. One such process for preparing 5-methoxy-2-aminotetralin is the reaction of 5-methoxy-2-tetralone (preparable from commercially available 1,6-dimethoxynaphthalene by a Birch reduction) with ammonia or an organic amine, followed if necessary by hydrogenation to convert the enamine or imine group on the tetralin nucleus to a free amine group.

The enzyme *Pseudomonas cepacia* lipase is known and commercially available. One commercial source from which it can be obtained is Altus Biologics Inc, under the trademark Chiro-CLEC-PC, cross-linked microcrystals of the lipase from *Pseudomonas cepacia*.

The acylating agent used in the present invention can be any acylating agent which is soluble in the chosen reaction medium (preferably in an organic aromatic solvent such as toluene), and which is capable of acylating the amino group on the aminotetralin to convert it to an amide group, under relatively mild conditions. Preferred acylating groups are lower alkyl esters of lower fatty acids, for example ethyl acetate.

The selectively acylated aminotetralin isomer thus produced, i.e. the amide, has a significantly increased molecular weight as compared with the non-acylated isomer, and a significantly altered chemical nature. Accordingly it can be separated therefrom by standard physico-chemical methods. Such method can be any of those known in the art which are capable of separating organic compounds on the basis of different molecular weight, for example chromatographic methods, gel elutions, fractional crystallizations, distillation and the like. Since the unchanged amine compound retains its basic characteristic from its amino group, whereas the amide formed as a result of acylation is neutral, the compounds can be separated by an acid-base extraction. Thus extraction of the the mixture of aminotetralin and its acylated isomer with an aqueous acid such as hydrochloric acid causes the aminotetralin to dissolve in the aqueous layer as the hydrochloride salt, while the acylated isomer remains dissolved in the organic phase.

The selective enzymatic acylation reaction according to the invention conveniently takes place in solution in an organic solvent such as toluene, benzene and the like, and at temperatures at which all of the reactants remain in solution in the liquid phase and which do not de-nature the enzyme. Temperatures in the range at 0–40° C. are suitable, with room temperatures being preferred.

The accompanying Figure diagrammatically illustrates the process. A mixture of the (S)-isomer of 5-methoxy-2-aminotetralin 10 and the (R)-isomer of 5-methoxy-2-aminotetralin 12 is reacted with ethyl acetate in the presence of a catalytic amount of the enzyme Pseudomonas cepacia lipase. The (R)-isomer is, as a result, selectively acylated at the amino group to give amide derivative 14. This derivative has a significantly increased molecular weight, as compared with the unchanged (S)-isomer, allowing its separation therefrom, and from the reaction mixture, by chromatographic methods.

The invention is further described, for illustrative purposes, in the following specific examples.

EXAMPLE 1

ChiroCLEL-PC (*Pseudomonas cepacia* lipase) catalyst (10 mg) was suspended in toluene (5 ml) and stirred at room temperature until an even suspension was formed. To this, a solution of 5-methoxy-2-aminotetralin (0.1 179 g, 0.552 mmol) dissolved in toluene (5 ml) was added. After stirring for 5 minutes, ethyl acetate (0.12 g, 1.35 mmol) was added. Analysis of the non-acylated aminotetralin was carried out by capillary electrophoresis using a Beckman Coulter P/ACE DMQ Capillary Electrophoresis System. Resolution of the mixture was achieved chromatographically using a 5% HS-α-cyclodextrin separation buffer on an eCAP Capillary Tubing (67 cm×50 μm I.D.). The control was found to contain 70% (S) and 30% (R) aminotetralin. After approximately 240 hours, 98% (S) and 2% (R) remained.

EXAMPLE 2

The racemic 2-amino-5-methoxytetralin was prepared from 5-30 methoxy-2-tetralone via hydrogenolysis of a 2-(N-benzylamino)-5-methoxytetralin as per literature procedure (J. Med. Chem., 1976, 547). The overall yield from the tetralone on assay basis was quantitative (112%).

ChiroCLEC-PC (Pseudomonas cepacia lipase, Altus #20) (0.49 g) was suspended in toluene (50 mL) at room temperature. To this, a solution of 2-amino-5-methoxytetralin (4.96 g, 28 mmol) in toluene (50 mL) was added. After stirring for 5 min, ethyl acetate (27 mL, 10 eq) was added. The reaction was monitored using capillary electrophoresis (CE) (Beckman Coulter P/ACE MDQ Capillary Electrophoresis System) using a 5% HS-α-cyclodextrin separation buffer on an eCAP Capillary Tubing (67 cm×50 pm I.D.). The reaction was worked up after 168 h, when the chromatogram showed only one peak of starting material, by filtering off the enzyme. The reaction mixture was evaporated to dryness and as diluted with $CH_2Cl_2$ (100 mL). The enantiomers were separated chemically. The organic phase was washed with 2 N HCl (3×100 mL). The organic phase was then dried ($MgSO_4$) and evaporated to dryness to obtain a greenish oil in 3.57 g (58%). The aqueous layer was basicified with solid NaOH and then extracted with $CH_2Cl_2$ (3×100 mL). After drying ($MgSO_4$), the solvent was removed to obtain a yellow oil. To this oil, a 20 mL of TBME was added and then HCl/IPA (3.94 M, 10 mL) to obtain a pinkish solid in 2.4 g (40%). This solid was recrystallized using EtOH/TBME to obtain white solid in 2.1 g (88%). The CE analysis for this material showed 100% of desired product. The HPLC purity (Zorbax SB-phenyl) showed 98.5%.

What is claimed is:

1. A process of isolating a stereoisomer of a carbocyclic amine compound from a mixture containing two or more such stereoisomers, which comprises subjecting the mixture to reaction with an acylating agent in the presence of the enzyme *Pseudomonas cepacia* lipase to effect selective acylation of one said stereoisomer whilst leaving other said stereoisomers substantially unchanged, and separating the selectively acylated carbocyclic amine stereoisomer from the reaction mixture.

2. The process of claim 1 wherein the carbocyclic amine is a carbocyclic compound having from 3–10 carbons in alicyclic structure optionally fused to one or more additional alicyclic or aromatic carbocyclic rings, the amine group being bonded to an alicyclic carbon to form a chiral center thereat.

3. The process of claim 2 wherein the carbocyclic amine is an aminotetralin, the aromatic ring portion thereof carrying one or more substituents selected from lower alkyl, lower alkoxy, halogen, cyano, lower alkylcarbonyl and lower alkoxycarbonyl.

4. The process of claim 3 wherein the aminotetralin compound is a lower alkoxy-substituted aminotetralin.

5. The process of claim 4 wherein the aminotetralin compound is 5-methoxy-2-aminotetralin.

6. The process of claim 3 wherein the acylating agent is a lower alkyl ester.

7. The process of claim 4 wherein the acylating agent is ethyl acetate.

8. The process of claim 3 which is conducted in solution in an aromatic organic solvent.

* * * * *